United States Patent [19]

Watanabe et al.

[11] Patent Number: 5,318,892
[45] Date of Patent: Jun. 7, 1994

[54] METHOD FOR ASSAYING ANTIBODY AGAINST CHLAMYDIA TRACHOMATIS AND DIAGNOSTIC PREPARATION FOR CHLAMYDIA TRACHOMATIS INFECTION

[75] Inventors: Hiroo Watanabe; Kiyotaka Kawagoe, both of Hitachi, Japan

[73] Assignee: Hitachi Chemical Co., Ltd., Tokyo, Japan

[21] Appl. No.: 62,699

[22] Filed: May 17, 1993

Related U.S. Application Data

[63] Continuation of Ser. No. 693,432, Apr. 29, 1991, abandoned.

[30] Foreign Application Priority Data

May 8, 1990 [JP] Japan ................................. 2-118012
Jan. 28, 1991 [JP] Japan ..................................... 3-8376

[51] Int. Cl.$^5$ .................. C12Q 1/00; G01N 33/53; G01N 33/566; G01N 33/567; G01N 33/563; C07K 3/00; C07K 13/00; C07K 15/00
[52] U.S. Cl. .................................. 435/7.36; 435/7.2; 435/7.21; 435/7.22; 435/7.92; 435/7.93; 435/7.94; 435/7.95; 436/513; 436/501; 436/503; 436/504; 530/350
[58] Field of Search ...................... 435/7.2, 7.21, 7.22, 435/7.36, 7.92, 7.93, 7.94, 7.95; 436/501, 503, 504, 513; 530/350

[56] References Cited

U.S. PATENT DOCUMENTS 4,427,782 1/1984 Caldwell et al. .
4,497,899 2/1985 Armstrong et al. .
4,663,291 5/1987 Rose .

FOREIGN PATENT DOCUMENTS 017460 10/1980 European Pat. Off. .
158725 3/1982 Japan .

OTHER PUBLICATIONS

Caldwell et al (Sep. 83) J Clin Mirobiol 18(3):539-545.
Brunham et al (Mar. 83) Infet & Immun 39(3) 1491-1494.
Peter (1986) The Use and Interpretation of Tests, Specialty Labs Inc.
Collett et al (1986) Abstract D-159 Abstracts of Annual Meeting of ASM.
Peter (1990) The Use and Interpretation of Test, Specialty Labs Inc pp. 26-27.
Miettinen et al (1990) J Clin Pathol 43(9): 758-760.
Cevenini et al (1986) J Clin Pathol 39:1313-1316.
Caldwell et al (1987) Infert & Immun 55(1) 93-98.
Poulettey et al (1988) J Clin Microbiol 26(2):267-270.
Cles et al (1988) J. Clin Microbiol 26(9):1735-1737.
Campbell et al, Infec. Immun., vol. 58, No. 1, 93-97 (1990).
Poulakkainen et al., J. Clin. Path., vol. 38, 929-932 (1985).
Mondesire et al., Infect. Immun., vol. 57, No. 9, 2914-2918 (1989).
Ward et al., J. of Gen. Microbiology, 132, 1599-1610 (1986).
Danilition et al., Infect. Immun., vol. 58, No. 1, 189-196 (1990).
Lema et al, J. of Immunol. Methods, vol. 94, 153-159 (1986).
Barron "Microbiology of *Chlamydia*", 48-50 (1988).
Laemmli, U.K. "Nature", 227, 680-685 (1970).
Caldwell et al., "Infection and Immunity", 31, 1161-1176 (1981).
Filip et al., "J. Bacteriology", 115, 717-722 (1973).

*Primary Examiner*—Esther L. Kepplinger
*Assistant Examiner*—David R. Preston
*Attorney, Agent, or Firm*—Abelman Frayne & Schwab

[57] ABSTRACT

There is provided an assay method for a *Chlamydia trachomatis* antibody with almost no cross reaction with a *C. pneumoniae* antibody or a *C. psittaci* antibody associated using an antigen containing at least two polypeptides which constitute *C. trachomatis* outer membranes.

17 Claims, 2 Drawing Sheets

METHOD FOR ASSAYING ANTIBODY AGAINST CHLAMYDIA TRACHOMATIS AND DIAGNOSTIC PREPARATION FOR CHLAMYDIA TRACHOMATIS INFECTION

This is a continuation of Ser. No. 693,432, filed Apr. 29, 1991, now abandoned.

BACKGROUND OF THE INVENTION

1. Field of the Invention

This invention relates to a method for assaying an antibody against *Chlamydia trachomatis* for the diagnosis of *C. trachomatis* infection and a diagnostic preparation used therefor.

*C. trachomatis* is a species of the obligatory intracellular parasite which can be alive only in cells of a host. The multiplication cycle of the species is unique. Morphologically, an extracellular chlamydial elementary body (EB) is introduced by phagocytosis into cells of a host, wherein they form a vacuole, inclusion. They are in turn metamorphosed to a reticulate body (RB), which are multiplicative but not infective. The intracellularly multiplied RB is then metamorphosed to EB which ruptures the inclusion, breaks the cell membrane of the host and comes out of the cell. The EB is infective but not multiplicative. If infected with the EB, the infected person will suffer from eye or genital diseases such as eye trachoma, lymphogranuloma venereum (LGV), nongonococcal urethritis (NGU) and cervicitis.

Recently our attention has been drawn to *C. trachomatis* as one of the causative microorganisms for sexually transmitted diseases. In the United States of America, 3 to 10 million fresh cases per year of C. infections are reported. Concern with C. infections is increasing also in Japan as the actualities of the infection have increasingly been known.

2. Description of the Prior Art

The most sensitive serological diagnosis for *C. trachomatis* is by the indirect microimmunofluorescent antibody technique (the micro-IF technique) developed by Wang and Grayston (see "Trachoma and related disorders caused by chlamydial agents", Excerpta Medica, Amsterdam, pp. 273-288, 1971). However, the micro-IF technique has not yet been employed as a diagnostic method in clinical laboratories because of technical difficulties in its operation. Standard micro-IF technique needs purified elementary, bodies (EB) of 15 different *C. trachomatis* serotypes. The entire morphology or structure of a microorganism to be identified is needed for immunofluorescent reaction in the micro-IF technique. Therefore, modification or breakdown of the morphology or structure of EB cannot be employed. Since the EB is infectious and toxic, use of intact EB as an antigen material requires a special institution with a protective equipment from the infection. Accordingly, an antigen treated with a fixing agent such as formaldehyde or acetone is usually employed.

On the other hand, a recently developed enzyme immunoassay method (ELISA) has an advantage of being capable of treating many test specimens rapidly and in a simple manner. Reports on the assay of a *C. trachomatis* antibody using the ELISA have appeared, most of which, however, use EB of strain L2 of *C. trachomatis*, either intact or treated with SDS (sodium dodecyl sulfate) as an antigen material. As a result, non-specific reactions are known to occur due to the use of an antigen of lower purity, including cross reactions with a *C. pneumoniae* antibody and a *C. psittaci* antibody. This is mainly attributed to complicated antigenicity of *C. trachomatis*. Antigenicity of *C. trachomatis* is believed to be due to three classes of antigens, genus specific antigen, species specific antigen and serotype specific antigen. Lipopolysaccharides (LPS) are known to be a typical genus specific antigen, which is common in antigenicity with Re mutant LPS of some intestinal microorganisms.

In addition, as a typical species specific or serotype specific antigen is known the major outer membrane protein (MOMP) of *C. trachomatis*, which is reported to constitute about 60% of the C. outer membrane protein. However, the MOMP is known to have some genus specific epitope (Colett et al., Annu. Meet. Am. Soc. Microbiol., Washington, D.C., Abstract No. D-159, 1986). *C. trachomatis* outer membrane antigens other than the MOMP are predominantly genus specific antigens, but some have species specific antigenicity simultaneously. Sarcosyl-insoluble peptide having a molecular weight of approximately 59.5 Kdaltons is in the latter category.

As described above, antigenicity of *C. trachomatis* is very complicated. A *C. trachomatis* antibody in *C. trachomatis* infected patients is multifaceted corresponding to such complicated antigenicity of *C. trachomatis* and varies in its pattern depending upon the patients. Consequently, it is practically impossible to employ a specified single C. antigen for the assay of a *C. trachomatis* antibody. Therefore, the antigen material to be employed needs to be properly selected in order to achieve an highly precise and sensitive assay of an anti-*C. trachomatis* antibody while inhibiting non-specific reactions, including cross reactions with a *C. pneumoniae* antibody and a *C. psittaci* antibody.

SUMMARY OF THE INVENTION

The present invention is directed to solving the problem of non-specific reactions including cross reactions with a *C. pneumoniae* antibody and a *C. psittaci* antibody which occur in the prior ELISA technique for the assay of a *C. trachomatis* antibody using the above-described EB, intact or SDS treated, as an antigen material. This is achieved by using as an antigen material a membrane fraction mainly composed of at least two polypeptides which constitute the outer membranes of *C. trachomatis*.

Thus, this invention relates to a method for assaying an antibody against *C. trachomatis* which is highly specific and less associated with non-specific reactions including cross reactions with a *C. pneumoniae* antibody and a *C. psittaci* antibody, said method comprising using an antigen containing at least two polypeptides which constitute the outer membranes of *C. trachomatis* and a diagnostic preparation for *C. trachomatis* infection comprising said antigen fixed on a solid carrier.

BRIEF DESCRIPTION OF THE DRAWING

In FIG. 1:

Figure 1:
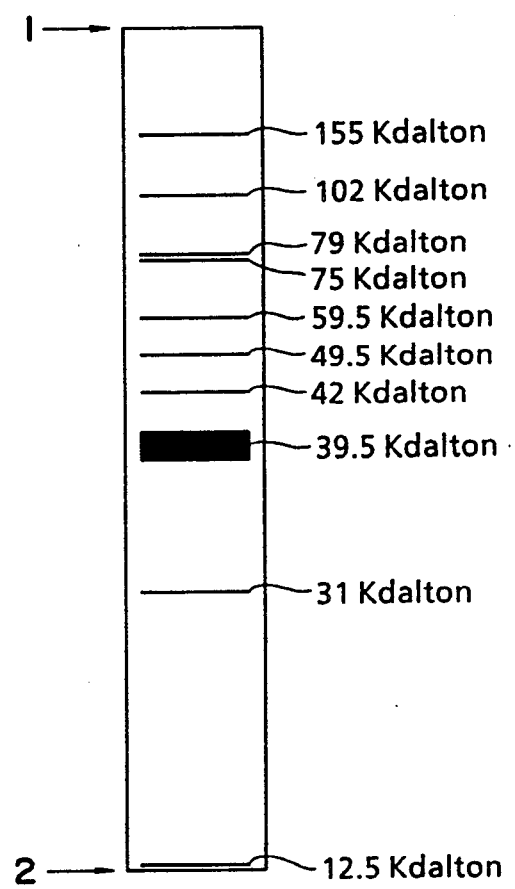
FIG. 1 is a pattern indicating the electrophoretic behaviors of a mixture of polypeptides of the *C. trachomatis* outer membrane on an SDS-polyacrylamide gel (behaviors on a 12.5% acrylamide slab gel).

1: Migration starting point.

2: Top of migration (Marker dye: BPB).

DETAILED DESCRIPTION OF THE INVENTION

The *C. trachomatis* outer membrane antigen used in the invention contains at least two polypeptides constituting *C. trachomatis* outer membrane and may be prepared by known methods such as one described by Caldwell et al. in Infection and Immunity, 31, 1161–1176, 1981.

Thus, *C. trachomatis* EB is purified by conventional methods, and the purified *C. trachomatis* EB is extracted with an ionic surfactant having a mild lowering activity of interfacial tension, preferably an anionic sarcosine surface active agent and especially preferably with sarcosyl (sodium N-lauroylsarcosine) to remove soluble constituents. There is prepared an unextracted constituent.

It is preferable that the product is subsequently subjected to a ribonuclease treatment with a DNase and an RNase.

To describe the invention more concretely, the purified *C. trachomatis* EB is extracted with PBS (pH 8.0) containing 2% sarcosyl and 1.5 mM EDTA to remove sarcosyl-soluble constituents followed by DNase-RNase treatment. There can be prepared a sarcosyl-insoluble fraction (unextracted constituent).

Originally, this method was developed for the preparation of outer membranes of *Escherichia coli*, a Gram-negative organism (Filip et al., J. Bacteriol. 115, 717–722, 1973). Morphological observation under an electronic microscopy of the *C. trachomatis* outer membrane complex thus obtained, which is composed of at least two polypeptides and lipid constituting *C. trachomatis* outer membrane, reveals that the complex is cell walls of *C. trachomatis* which have been formed by losing cytoplasmas and cytoplasmic membranes from the whole cell (EB) of *C. trachomatis*. Accordingly, the *C. trachomatis* outer membranes are similar in structure and function to the outer membranes (cell walls) of Gramnegative bacteria.

The *C. trachomatis* outer membrane complex (sarcosyl-insoluble fraction) obtained as above can be employed as the antigen of the present invention. However, it is solubilized with an ionic surfactant having a stronger lowering activity of interfacial tension than the above-employed one, preferably with sodium dodecyl sulfate (SDS) in order to produce an antigen more suitable for use in the invention. Thus, there is produced a mixture of at least two polypeptides of *C. trachomatis* outer membrane for use as the antigen in the invention.

The mixture of the polypeptides of *C. trachomatis* outer membrane, as analyzed by SDS polyacrylamide electrophoresis under the conditions described below, contains ca. 155 Kdaltons, ca. 102 Kdaltons, ca. 79 Kdaltons, ca. 75 Kdaltons, ca. 59.5 Kdaltons, ca. 49.5 Kdaltons, ca 42 Kdaltons, ca. 39.5 Kdaltons, ca. 31 Kdaltons, ca. 12.5 Kdaltons, etc. The polypeptide of ca. 39.5 Kdaltons represents about 60% of the entire peptides and is called major outer membrane peptide (MOMP). On the other hand, the peptide of ca. 12.5 Kdaltons is a cysteinerich peptide which is specific to the species *C. trachomatis* but does not occur in the species *C. psittaci* (Barron, Microbiology of Chlamydia, CRC Press Inc., Boca Raton, Florida, 48–50, 1988). It has also been found that the peptide of ca. 59.5 Kdaltons exhibits genus specific antigenicity.

In the present invention, it is preferable to use as an antigen the above-prepared outer membrane complex of *C. trachomatis* containing a variety of peptides as it is, but a mixture containing at least two peptides of the above-cited molecular weights of a *C. trachomatis* outer membrane may also be used as an antigen. If IgG or IgA is employed as an antibody in the latter case, an antigen preferably contains peptides of ca. 39.5 Kdaltons (MOMP) and ca. 59.5 Kdaltons. If IgM is employed as an antibody, an antigen preferably contains peptides of ca. 75 Kdaltons and ca. 59.5 Kdaltons. The molecular weight of peptides referred to herein is expressed in approximate numerical value in view of possible errors occurring in every measurement. Furthermore, although peptides may exhibit a molecular weight of a value different from the mentioned one depending on conditions for the molecular weight measurement by SDS electrophoresis, peptides having a molecular weight defined in the invention will cover the former if the two are identical.

It is important in the invention to use an antigen containing at least two of the above-mentioned polypeptides of a *C. trachomatis* outer membrane. If a single polypeptide, for example, purified to ca. 39.5 Kdalton peptide (MOMP) is used, there will occur a pseudonegative reaction which is problematic from a clinical point of view, or species specificity will hardly be sufficient.

In the present preparations, the antigen is fixed using as a solid carrier a plastic material such as polystyrene or -vinyl chloride, a fibrous material such as nitrocellulose or nylon and an inorganic material such as glass or silica gel. These materials may be in various forms including a titer plate, beads, magnetic beads, a paper disc and threads. Preferably used among them are polystyrene beads and a polystyrene microtiter plate. In addition to the solid phase formation by means of physical adsorption on a solid carrier as mentioned above, the preparation of the invention may also be, in principle, of a solid phase in which an antigen material is covalently bound to a carrier using, for example, $BrCN_2$.

In the assay of a human *C. trachomatis* antibody using the present preparation, human serum is used as specimen in the majority of tests. However, the method of the invention can also be applied to test specimens of a low *C. trachomatis* antibody titer because non-specific reactivity is lower. Accordingly, human tear, a secretion from internal membranes of the human uterocervical canal, an expressed prostatic secretion and human sperma can also be a test specimen.

The solid phase carrier with an antigen fixed thereon as described above is contacted with a properly diluted test specimen suspected of containing an antibody against *C. trachomatis* followed by incubation for a predetermined period of time thereby allowing the two to react. Unreacted components of the specimen are removed to give on the carrier a complex of the antigen of *C. trachomatis* outer membrane and the antibody of *C. trachomatis*. The antigen/antibody complex is then reacted by contact with a labeled antibody to the antibody originated from the test specimen, preferably an enzyme-labeled anti-human IgG, IgA or IgM antibody. Unreacted labeled antibody is then removed, and a quantity of the bound labeling substance on the labeled antibody is assayed to determine the IgG, IgA or IgM of *C. trachomatis* antibody present in the test specimen.

The labeling substance need not be limited to enzymes but may include radioactive isotopes, fluorescent dyes and others. As the labeling enzyme there may be employed maleate dehydrogenase (EC No. 1.1.1.37), glucose-6-phosphate dehydrogenase (EC No. 1.1.1.49), glucose oxidase (EC No. 1.1.3.4), horseradish peroxidase (EC No. 1.11.1.7), acetylcholine esterase (EC No. 3.1.1.7), alkaline phosphatase (EC No. 3.1.3.1), β-glucoamylase (EC No. 3.2.1.3), 3.2.1.23), etc. Preferably alkaline phosphatase or horseradish peroxidase is used. Assay of the labeling substance can be carried out by conventional methods selected depending on the nature of the labeling substance.

It has been demonstrated, that the *C. trachomatis* antibody titer thus determined will reflect clinical signs of *C. trachomatis* infections. Thus, it is believed that an IgM antibody appears 1-2 weeks after *C. trachomatis* infection on body surface and that an IgG antibody appears also at an earlier stage, decreases with time, but is durable for a long period of time. On the other hand, the IgA antibody of secretional type is believed to be effective for preventing recurrence of the infection as is cellular immunity. In genital *C. trachomatis* infections in humans, particularly in females, it is known that the IgG, IgA and IgM antibodies are detected in serum and secretions from internal membranes of the uterocervical canal, and that the amount of the IgA antibody is reversely proportional to the decrease of pathogenic parasites of *C. trachomatis* and controls excretion and diffusion of the pathogenic parasites (Brunham et al., Infect. Immun., 39, 1491-1494, 1983).

EXAMPLES

The present invention will be described in more detail below regarding isolation of the outer membrane complex or the mixture of at least two polypeptides of *C. trachomatis*, its fixation on a solid carrier and a method for assaying an *C. trachomatis* antibody. It is not intended, however, that the invention is limited thereto.

A) Purification of elementary bodies (EB) of *C. trachomatis*.

Strain L2/434/Bubo of *C. trachomatis* was used. The strain was inoculated into McCoy cells propagated in an Eagle MEM medium containing 10% fetus bovine serum (FBS). For the inoculation with *C. trachomatis* were used the cells which had been cultivated for 3 days, collected by centrifugation at 150×g for 5 min. and washed three times by centrifugation with a Hank's BSS. Adsorption of *C. trachomatis* was effected by shaking 10 parasites per cell of the host in water at 37° C. for 2 hours at a host cell concentration of $10^7$/ml After the adsorption process the cells were resuspended to a cell concentration of 5-7×$10^5$/ml in the FBS-containing medium followed by culture at 37° C. for 2 days. After the culture was completed, a portion of the culture was removed and centrifuged to collect infected cells. A smear sample of the cells was prepared and examined by the Giemsa staining for sufficient propagation of the EB.

The above-prepared suspension of the infected cultured cells was subjected to supersonic disintegration at 20 KHz for 60 sec. in a supersonic disintegrator (US-300, manufactured by K.K. Nippon Seiki Seisakusho) and then centrifuged at 20° C. for 20 min. to collect a supernatant of the infection culture. Five volumes of the supernatant was superposed upon one volume of a 0.033 M tris-HCl buffer solution (pH 7.2) containing 30% (w/v) sucrose followed by centrifugation at 10,000×g at 4° C. for 60 min. The precipitates from the centrifugation were suspended in a 0.01 M sodium phosphate buffer solution (PBS) (pH 7.2) containing 0.14 M sodium chloride, and the suspension superposed upon a 0.01 M HEPES (N-2-hydroxyethylpiperazine-N'-2-ethanesulfonic acid) solution containing 35% urografin (diatrizoate meglumine and trizate sodium) and 0.15 M sodium chloride followed by centrifugation at 43,000×g at 4° C. for 60 min. (Separative ultracentrifuge 70P-72, Swingrotor SPR 28SA manufactured by Hitachi Koki K.K.). The precipitates were suspended in a 0.01 M sodium phosphate buffer solution (SPG, pH 7.2) containing 0.25 M sucrose and 5 mM glutamic acid, and the suspension superposed on urografin at a discontinuous density gradient (40%/44%/52%) followed by centrifugation at 43,000×g at 4° C. for 60 min. Precipitate zone of the EB formed on the interface between the 44% and 52% urografins was recovered and diluted with SPG. Purified EB was produced by repeated centrifugations at 30,000×g at 4° C. for 30 min. to remove the residual urografin.

B) Purification of the *C. trachomatis* outer membrane antigen

The purified EB of *C. trachomatis* strain L2 was suspended in a 0.01 M sodium phosphate buffer solution containing 2% sarcosyl (N-lauroylsarcosine sodium salt), 1.5 mM EDTA (ethylenediamine tetraacetic acid) and 0.14 M sodium chloride (sarcosyl buffer solution, pH 8.0), and the suspension subjected to supersonic disintegration at 20 KHz for 60 sec., allowed to stand at 37° C. for one hour and then centrifuged at 100,000×g at 20° C. for 60 min. After the centrifugation process, the precipitates were resuspended in a small amount of the same sarcosyl buffer solution as mentioned above, and the suspension centrifuged at 100,000×g at 20° C. for 60 min. Excess sarcosyl in the precipitates was removed by washing twice with PBS (pH 8.0). The washed precipitates were then suspended in a 0.02 M sodium phosphate buffer solution (pH 8.0) containing 10 mM $MgCl_2$ in which DNase and RNase had been dissolved respectively at 2.5 μg/ml. The suspension was allowed to stand at 37° C. for 2 hours and then centrifuged at 100,000×g at 4° C. for 60 min. Residual DNase and RNase in the precipitates were removed by washing twice with PBS (pH 8.0). There were produced sarcosyl-insoluble polypeptides constituting the outer membranes of *C. trachomatis* (*C. trachomatis* outer membrane complex).

In order to solubilize the *C. trachomatis* outer membrane complex, it was suspended in a 0.01 M sodium phosphate buffer solution (pH 6.4) containing 2% SDS (sodium dodecylsulfate) and 10 mM DTT (dithiothreitol), the suspension allowed to stand at 37° C. for one hour and then centrifuged at 100,000×g at 20° C. for 60 min., and the supernatant dialyzed overnight against a 0.01 M sodium phosphate buffer solution (pH 6.4) containing 0.1% SDS and 1 mM DTT. There was prepared an SDS-solubilized outer membrane complex of *C. trachomatis*, a mixture of polypeptides of *C. trachomatis* outer membrane. FIG. 1 shows an SDS polyacrylamide gel electrophoresis pattern of a mixture of the polypeptides of *C. trachomatis* outer membrane.

As clearly seen from FIG. 1, the mixture of polypeptides of *C. trachomatis* outer membrane contains 155 Kdalton peptide (Rf 0.12), 102 Kdalton peptide (Rf 0.18), 79 Kdalton peptide (Rf 0.26), 75 Kdalton peptide (Rf 0.27), 59.5 Kdalton peptide (Rf 0.33), 49.5 Kdalton peptide (Rf 0.38), 42 Kdalton peptide (Rf 0.43), 39.5

Kdalton peptide (Rf 0.49), 31 Kdalton peptide (Rf 0.67) and 12.5 Kdalton peptide (Rf 0.99).

The SDS polyacrylamide gel electrophoresis was carried out as follows:

An electrophoresis was carried out in a 12.0% acrylamide gel (degree of cross linking, 0.8) according to the method of Laemmli (Laemmli, U.K. Nature, 227, 680–685, 1970). Electrophoretic conditions were at 15 mA during concentration electrophoresis and at 20 mA during separation electrophoresis. To the sample for migration was in advance added as a reducing agent 0.25 volume of a buffer solution for electrophoresis sample [312.5 mM Tris-hydrochloric acid, pH 6.8, 0.1% BPB (bromphenol blue), 10% SDS, 20% glycerin], and the mixture treated at 50° C. for 30 min. The gel after migration was stained with 0.05% Coomassie R-250 overnight at room temperature and discolored with 0.7% acetic acid. The molecular weight was estimated in comparison with the mobility of molecular weight-marker protein (Markers: Rabbit muscle phosphorylase 97.4 KDa, bovine serum albumin 66.2 KDa, ovalbumin 42.7 KDa, bovine decarboxylase 31 KDa, soybean trypsin inhibitor 21.5 KDa and albumen lysozyme 14.4 KDa).

C) Method for assaying *C. trachomatis* antibody

A solution of the SDS-solubilized outer membrane of *C. trachomatis* prepared above (a mixture of polypeptides of *C. trachomatis* outer membrane) in a carrier fixing buffer solution (containing 2.93 g of NaHCO and 1.59 g of $Na_2CO_3$ per liter) at 0.5 µg/ml was divided into wells of a 96-well polystyrene microtiter plate in a volume of 100 µl per well and allowed to react overnight at 4° C. Each of the wells was washed three times with 300 µl of PBS (pH 7.2) containing 0.05% Tween 20 (0.05% Tween 20-PBS) to remove the unadsorbed antigen. To each of the wells was then added 250 µl of a blocking buffer solution containing 5% BSA (manufactured by KPL) (a buffer solution for blocking/dilution of test specimen) followed by reaction at 37° C. for one hour. Each of the plate was washed twice with 300 µl of 0.05% Tween 20-PBS. There was prepared an antigen-fixed plate.

To each of the wells of the antigen-fixed plate was added 100 µl of a serum specimen diluted with the buffer solution for blocking/dilution of test specimen followed by reaction at 37° C. for one hour. Each of the wells was washed three times with 300 µl of 0.05% Tween 20-PBS. An anti-human IgG antibody labeled with horseradish peroxidase was diluted with 0.05% Tween 20-PBS to 1 µl/ml and divided into the wells so as to contain 100 µl of the antibody per well. The wells were allowed to react at 37° C. for one hour, and then washed three times with 300 µl of 0.05% Tween 20-PBS per well followed by addition of 100 µl of ABTS reagent (manufactured by KPL), a substrate for peroxidase per well. The mixture was then allowed to react at room temperature for 5 min. followed by the addition of 25 µl of 2% oxalic acid per well to terminate the reaction. Measurement of the absorbancy ($\lambda_1$: 415 nm, $\lambda_2$: 492 nm) was made by means of a microtiter plate reader (Model MTP-22, Corona Electric Co. Ltd.).

D) Sensitivity and specificity to serums of human patients (assay of an anti-*C. trachomatis* IgG antibody)

Figure 2:
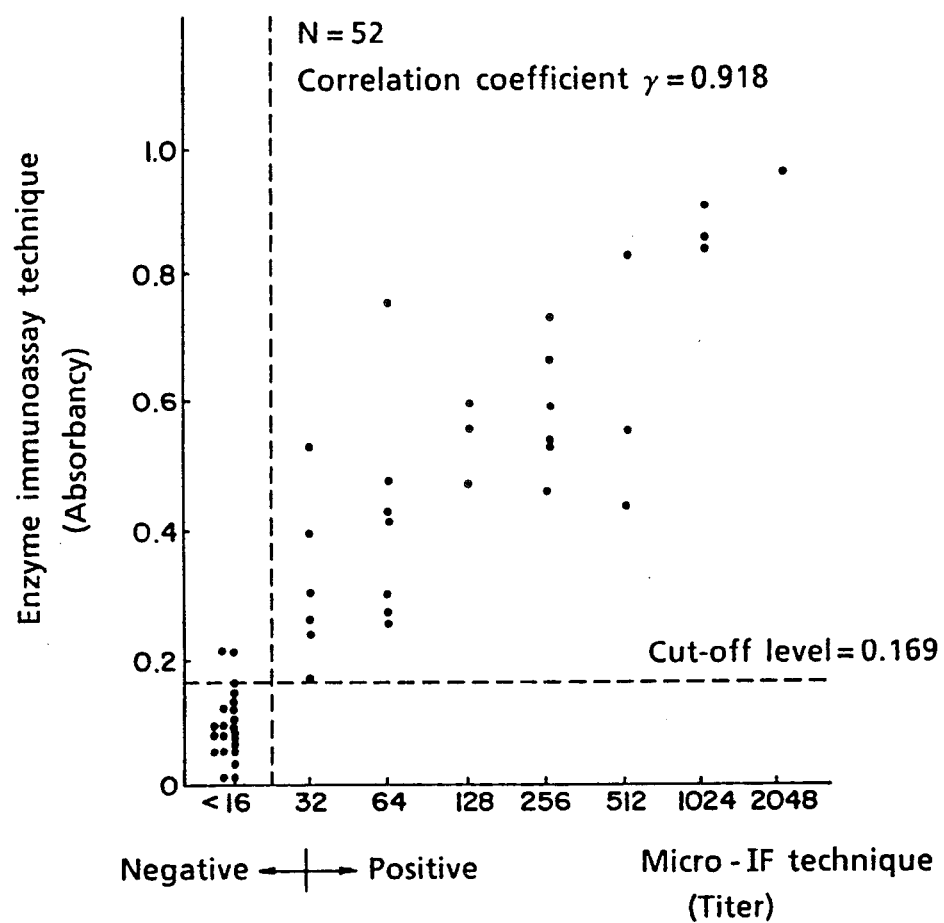
FIG. 2 is a graph indicating the correlation between the enzyme immunoassay technique (ELISA) using a mixture of the polypeptides of *C. trachomatis* outer membranes as an antigen and the micro-IF technique.

A sensitivity and specificity test was carried out with 20 serum specimens from *C. trachomatis* infected patients from whom the parasite had been isolated (antigen positive), 9 serum specimens from *C. trachomatis* antibody positive patients (antigen negative) and 23 serum specimens from normal persons according to the measurement described under C) (ELISA technique). As a comparative test method was employed the micro-IF technique. The human serum was 1:80 diluted with a buffer solution for dilution of a test specimen containing 0.1% BSA to prepare a specimen solution for the assay of *C. trachomatis* antibodies. Results of the assay is shown in FIG. 2. The results are presented in terms of the absorbance at 415 nm for the ELISA technique and of the multiple of dilution (titer) for the micro-IF technique.

In order to demonstrate the effect of the invention more clearly, comparisons were made of sensitivity and specificity between purified EB of *C. trachomatis* strain L2 (purified EB) or purified major outer membrane peptides of *C. trachomatis* (purified MOMP) as a control antigen and the mixture of polypeptides of *C. trachomatis* outer membrane used in the invention. The results are shown in Table 1. The purified EB was prepared as previously described. As the purified MOMP was used an immunologically uniform material produced by preparing a partially purified MOMP fraction according to the method of Caldwell, H. D. et al. (Japanese Patent Application Laid-Open-to-Public No. 158725/1982) and further subjecting the MOMP fraction to preparative SDS polyacrylamide gel electrophoresis. The cut-off level was set for a value obtained by adding standard deviation multiplied by two to an average absorbance for 23 serum specimens from normal persons.

The results in FIG. 2 indicate that the results produced by the assay method of the invention are in very good correlation with those with the prior micro-IF technique.

The results in Table 1 also indicate that the method of the invention in which a mixture of polypeptides of *C. trachomatis* outer membrane is used is much superior in correspondence with the micro-IF technique to the purified EB or the purified MOMP tested as a control antigen. In the former method, there are observed very low false positive, and especially no false negative which is clinically problematic. This indicates that the present assay method is of high clinical usefulness.

TABLE 1

| | Test item | | |
|---|---|---|---|
| Used antigen | Percent correspondence in positive serum (Sensitivity) (Positve specimens = 29) | Percent correspondence in negative serum (Specificity) (Negative specimens = 23) | Cut-off level |
| Mixture of polypeptide of C. outer membrane | 100% (29) | 91% (21) | 0.169 |
| Control | | | |
| Purified EB | 93% (27) | 100% (23) | 0.278 |
| Purified MOMP | 62% (18) | 100% (23) | 0.111 |

E) Cross reactivity with *C. pneumoniae* antibody or *C. psittaci* antibody

A cross reactivity test was carried out using 7 serum specimens from *C. trachomatis* antibody positive patients, 17 serum specimens from *C. pneumoniae* antibody positive patients and 2 serum specimens from *C. psittaci* antibody positive patients according to the assay method described under C) (ELISA technique). As a comparative test method was employed MFA technique (microplate immunofluorescence antibody technique). A specimen solution for the assay of a *C. trachomatis* antibody was prepared by diluting, before use, the human serum with a buffer solution for dilution of the specimen containing 1% BSA 100 times for the assay of an IgG antibody or 20 times for an IgA antibody. Results of the assay are shown in Table 2. Data are shown in terms of the absorbance at 415 nm for the ELISA technique and of the multiple of dilution (potency) against *C. pneumoniae* strain TW, *C. psittaci* strain MP and *C. trachomatis* strain L2 for the MFA technique.

Table 2 shows that the results of the assay method of the invention very highly correspond to those with the prior MFA technique, that is, there is almost no cross reaction with a *C. pneumoniae* antibody as well as with a *C. psittaci* antibody.

The cut-off level was set so that values higher than 0.15 for the assay of IgG antibodies and 0.20 for the assay of IgA antibodies are judged as positive.

and a lipid, and determining the specific binding of said antibody to said antigen in said sample.

2. The method according to claim 1 wherein the antigen contains polypeptides having a molecular weight of ca. 155 Kdal, ca. 102 Kdal, ca. 79 Kdal, ca. 75 Kdal, ca 59.5 Kdal, ca. 49.5 Kdal, ca. 42 Kdal, ca. 39.5 Kdal, ca. 31 Kdal, and ca. 12.5 Kdal, and a lipid.

3. A method for assaying an antibody against *C. trachomatis* in a sample comprising contacting said sample suspected of containing an antibody against *C. trachomatis* with an antigen consisting of a mixture of *C. trachomatis* outer membrane-constituting polypeptides consisting essentially of at least three polypeptides having a molecular weight of ca. 75 Kdaltons, ca. 59.5 Kdaltons and ca. 39.5 Kdaltons, and determining the specific binding of said antibody to said antigen in said sample.

4. The method according to claim 3 wherein the mixture contains polypeptides having a molecular weight of ca. 155 Kdaltons, ca. 102 Kdaltons, ca. 79 Kdaltons, ca. 75 Kdaltons, ca. 59.5 Kdaltons, ca. 49.5

TABLE 2

| Antibody | Specimen | | | MFA | | | | | | ELISA | |
|---|---|---|---|---|---|---|---|---|---|---|---|
| | | | | IgG | | | IgA | | | | |
| | No. | Sex | Age | TW | MP | L2 | TW | MP | L2 | IgG | IgA |
| *C. trachomatis* | 1 | F | 43 | 512 | 256 | 1024≦ | 64 | <16 | 128≦ | 0.644 | 0.884 |
| | 2 | F | 21 | 512 | 128 | 1024≦ | 32 | <16 | 128≦ | 0.875 | 0.683 |
| | 3 | M | 20 | 256 | 128 | 1024 | 16 | <16 | 128≦ | 0.256 | 0.657 |
| | 4 | F | 0 | 32 | <32 | 1024 | <16 | <16 | 128 | 0.478 | 0.457 |
| | 5 | M | 43 | 64 | 64 | 1024 | <16 | <16 | 64 | 0.335 | 0.350 |
| | 6 | M | 8 | 256 | 256 | 1024 | 64 | 16 | 128≦ | 0.352 | 0.394 |
| | 7 | F | 23 | 128 | 128 | 1024 | 32 | 32 | 128 | 0.407 | 0.392 |
| *C. pneumoniae* | 1 | M | 76 | 512 | <32 | 32 | 64 | <16 | <16 | 0.053 | 0.129 |
| | 2 | M | 56 | 256 | 64 | 64 | 32 | <16 | <16 | 0.037 | 0.069 |
| | 3 | M | 17 | 256 | <32 | <32 | 32 | <16 | <16 | 0.044 | 0.033 |
| | 4 | M | 64 | 256 | <32 | 128 | 32 | <16 | <16 | 0.073 | 0.051 |
| | 5 | M | 42 | 256 | 64 | 128 | 16 | <16 | <16 | 0.213 | 0.136 |
| | 6 | M | 33 | 512 | 32 | 64 | 64 | <16 | <16 | 0.090 | 0.057 |
| | 7 | M | 21 | 512 | 32 | 32 | 16 | <16 | <16 | 0.078 | 0.019 |
| | 8 | M | 61 | 512 | <32 | <32 | 32 | <16 | <16 | 0.051 | 0.026 |
| | 9 | F | 60 | 256 | <32 | <32 | 16 | <16 | <16 | 0.056 | 0.054 |
| | 10 | M | 12 | 512 | 32 | <32 | 32 | <16 | <16 | 0.079 | 0.106 |
| | 11 | F | 29 | 512 | 32 | <32 | 64 | <16 | <16 | 0.075 | 0.078 |
| | 12 | M | 36 | 256 | 128 | 128 | 16 | <16 | <16 | 0.049 | 0.090 |
| | 13 | M | 13 | 1024 | 32 | 32 | 64 | <16 | <16 | 0.065 | 0.152 |
| | 14 | M | 75 | 1024 | 64 | 256 | 128≦ | <16 | 32 | 0.067 | 0.060 |
| | 15 | M | 53 | 1024 | <32 | 512 | 64 | <16 | <16 | 0.173 | 0.159 |
| | 16 | M | 66 | 1024 | 64 | 256 | 128≦ | <16 | 16 | 0.145 | 0.145 |
| | 17 | M | 71 | 512 | 64 | <32 | 128≦ | <16 | <16 | 0.072 | 0.102 |
| *C. psittaci* | 1 | M | 18 | 128 | 256 | 64 | <16 | 64 | <16 | 0.059 | 0.173 |
| | 2 | F | 40 | 128 | 256 | 32 | 32 | 64 | <16 | 0.061 | 0.185 |

*M: Male, F: Female

As clearly seen from the above, highly species-specific assay of *C. trachomatis* can be carried out according to the method of the invention without clinically problematic false negative and with much lower false positive observed and further with almost no non-specific reaction with a *C. pneumoniae* antibody or a *C. psittaci* antibody associated as compared with the assay method using purified EB or purified MOMP. Therefore, the method of the invention is more highly useful in clinical applications.

What is claimed is:

1. A method for assaying an antibody against *Chlamydia trachomatis* in a sample comprising contacting said sample suspected of containing an antibody against *C. trachomatis* with an antigen consisting of a *C. trachomatis* outer membrane complex consisting essentially of at least three polypeptides having a molecular weight of ca. 75 Kdaltons, ca. 59.5 Kdaltons and ca. 39.5 Kdaltons Kdaltons, ca. 42 Kdaltons, ca. 39.5 Kdaltons, ca. 31 Kdaltons and ca. 12.5 Kdaltons.

5. A method for assaying an antibody against *C. trachomatis* which comprises the steps of:

(a) fixing on a solid carrier an antigen consisting of a *C. trachomatis* outer membrane complex consisting essentially of at least three polypeptides having a molecular weight of ca. 75 Kdaltons, ca. 59.5 Kdaltons and ca. 39.5 Kdaltons and a lipid or an antigen consisting of a mixture of *C. trachomatis* outer membrane-constituting polypeptides consisting essentially of at least three polypeptides having a molecular weight of ca. 75 Kdaltons, ca. 59.5 Kdaltons and ca. 39.5 Kdaltons, (b) contacting said solid carrier with a test specimen suspected of containing an antibody against *C. trachomatis*, (c) removing unreacted components of said test specimen, (d) contacting the thus formed antigen-antibody complexes consisting essentially of the *C. trachomatis* outer membrane antigen and the antibody against *C. trachomatis* with a labeled antibody against the antibody originating from said test specimen, (e) removing the unreacted portion of said labeled antibody, and (f) measuring a quantity of the labeling substance bound on said labeled antibody to determine the presence or quantity of the antibody against *C. trachomatis* in the test specimen.

6. The method for assaying the antibody according to claim 5 wherein the test specimen is one selected from the group consisting of human tear, a secretion from internal membranes of the human uterocervical canal, human sperma and human serum.

7. The method for assaying the antibody according to claim 5 wherein the labeled antibody is an anti-human IgG, IgA or IgM antibody.

8. The method for assaying the antibody according to claim 5 wherein the labeled antibody is an enzyme-labeled antibody.

9. The method for assaying the antibody according to claim 8 wherein the enzyme-labeled antibody is an antibody labeled with alkaline phosphatase or horseradish peroxidase.

10. A diagnostic preparation for *C. trachomatis* infection which comprises an antigen consisting of a *C. trachomatis* outer membrane complex consisting essentially of at least three polypeptides having a molecular weight of ca. 75 Kdaltons, ca. 59.5 Kdaltons and ca. 39.5 Kdaltons and a lipid, or an antigen consisting of a mixture of *C. trachomatis* outer membrane-constituting polypeptides consisting essentially of at least three polypeptides having a molecular weight of ca. 75 Kdaltons, ca. 59.5 Kdaltons and ca. 39.5 Kdaltons fixed on a solid carrier.

11. The diagnostic preparation for *C. trachomatis* infection according to claim 10 wherein the solid carrier is selected from the group consisting of plastic materials, fibrous materials and inorganic materials.

12. The diagnostic preparation for *C. trachomatis* infection according to claim 10 wherein the solid carrier is polystyrene beads or a polystyrene microtiter plate.

13. The diagnostic preparation for *C. trachomatis* infection comprising, in combination, the fixed antigen according to claim 10 and anti-human IgG, IgA or IgM antibody as a labeled antibody.

14. The diagnostic preparation for *C. trachomatis* infection according to claim 13 wherein the labeled antibody is an enzyme-labeled antibody.

15. The diagnostic preparation for *C. trachomatis* infection according to claim 14 wherein the labeled antibody is an alkaline phosphatase- or horseradish peroxidase-labeled antibody.

16. The method for assaying the antibody according to claim 1, wherein the antigen is obtained by extracting purified *C. trachomatis* elementary bodies with an ionic surfactant having a mild lowering activity of interfacial tension to remove soluble constituents.

17. The method for assaying the antibody according to claim 3 wherein the antigen is obtained by extracting purified *C. trachomatis* EB with a first ionic surfactant having a mild lowering activity of interfacial tension to remove soluble constituents, and solubilizing the extracting residue with a second ionic surfactant having a stronger lowering activity of interfacial tension than said first ionic surfactant.

* * * * *